(12) United States Patent
Higgins et al.

(10) Patent No.: US 8,068,218 B2
(45) Date of Patent: Nov. 29, 2011

(54) WATER IN OIL MEASUREMENT USING STABILIZER

(75) Inventors: Frank S. Higgins, Naugatuck, CT (US); John A. Seelenbinder, Watertown, CT (US)

(73) Assignee: Agilent Technologies, Inc., Santa Clara, CA (US)

( * ) Notice: Subject to any disclaimer, the term of this patent is extended or adjusted under 35 U.S.C. 154(b) by 235 days.

(21) Appl. No.: 12/422,817

(22) Filed: Apr. 13, 2009

(65) Prior Publication Data

US 2009/0257047 A1    Oct. 15, 2009

Related U.S. Application Data

(60) Provisional application No. 61/044,502, filed on Apr. 13, 2008.

(51) Int. Cl.
*G01N 33/28* (2006.01)
(52) U.S. Cl. .......................................................... 356/70
(58) Field of Classification Search .................. 356/70, 356/332–343
See application file for complete search history.

(56) References Cited

U.S. PATENT DOCUMENTS

| | | | |
|---|---|---|---|
| 3,648,770 A | 3/1972 | Sydansk et al. | |
| 4,434,233 A | 2/1984 | Bzdula | |
| 5,306,909 A * | 4/1994 | Jones et al. | 250/255 |
| 5,381,002 A * | 1/1995 | Morrow et al. | 250/301 |
| 2008/0280791 A1 | 11/2008 | Hewette | |
| 2009/0194480 A1 | 8/2009 | McDaniel et al. | |

FOREIGN PATENT DOCUMENTS

| | | |
|---|---|---|
| EP | 1990400 A2 | 11/2008 |
| EP | 2000130 A1 | 12/2008 |
| WO | 2009074815 A2 | 6/2009 |
| WO | 2009099687 A1 | 8/2009 |

OTHER PUBLICATIONS

Zou Hua-Sheng et al., Japanese Abstract of Stability Analysis of Water-in-Oil Microemulsion System, Journal of South China, University of Technology, Natural Science Edition, vol. 36, No. 3, pp. 32-36, 2008.
Stig E. Friberg, et al., Geranyl acetate emulsions: Surfactant association structures and emulsion inversion, Journal of Colloid and Interface Science 336, pp. 345-351, 2009.
M. Adam, et al., Combination of Solid Phase Extraction With Supercritical Fluid Extraction for the Determination of Contaminants in Water, Journal of Liquid Chromatography and Related Technologies, vol. 23, pp. 1511-1522, 2000.
Irene M. Goncalves, et al., Determination of metals in used lubricating oils by AAS using emulsified samples, Talanta, vol. 47, pp. 1033-1042, 1998.
Matthew F. Smiechowski, et al., Electrochemical monitoring of water-surfactant interactions in industrial lubricants, Journal of Electroanalytical Chemistry, vol. 534, pp. 171-180, 2002.

(Continued)

*Primary Examiner* — Michael P Stafira (57) ABSTRACT

A method for determining an amount of polar substance in a non-polar media includes adding a surfactant to increase a dispersion of the polar substance in the non-polar media and to increase the optical absorbance of the polar substance in the non-polar media to create a sample, passing an initial optical spectrum through the sample, measuring a resultant optical spectrum exiting the sample, relating the resultant optical spectrum to a predetermined quantitative calibration, and determining a concentration of the polar substance in the non-polar media based on the relation of the resultant optical spectrum to the quantitative calibration.

21 Claims, 7 Drawing Sheets

OTHER PUBLICATIONS

W. Zhou, et al., Experimental Investigation of Surfactant Partition in Heavy Oil/Water/Sand Systems, Petroleum Science and Technology, vol. 26, pp. 1036-1046, 2008.

Duncan J. McGillivray, et al., Nano-and Microstructure of Air/Oil/Water Interfaces, Langmuir, vol. 25, pp. 4065-4069, 2009.

Rawad Tadmouri, et al., Partition and Water/Oil Adsorption of Some Surfactants, Journal of Physical Chemistry B, vol. 112, pp. 12318-12325, 2008.

Michihiro Nagao, et al., Full fitting analysis of the relative intermediate form factor measured by neutron spin echo, Physica B, vol. 404, pp. 2603-2606, 2009.

K. Altria, Preliminary Study on the Use of Water-in-Oil Microemulsion Eluents in HPLC, Chromatographia, vol. 62, pp. 341-348, 2005.

Keiichi Honda, et al., Properties, application and nuclear magnetic resonance spectroscopic study of some new non-ionic surface active agents useful in formulation of water-in-oil emulsions, Journal of the Society of Cosmetic Chemists, vol. 32, pp. 255-273, Sep./Oct. 1981.

Ricardo Cantu, et al., Surfactant-Enhanced Partitioning of Nickel and Vanadyl Deoxophylloerythroetioporphyrins from Crude Oil into Water and Their Analysis Using Surfactant-Enhanced Resonance Raman Spectroscopy, Environmental Science and Technology, vol. 34, pp. 192-198, 2000.

* cited by examiner

WATER IN OIL MEASUREMENT USING STABILIZER

This application claims the benefit of U.S. Provisional Application No. 61/044,502, filed Apr. 13, 2008, which is hereby incorporated by reference.

BACKGROUND

The present invention relates to measuring a polar substance in a non-polar media. It finds particular application in conjunction with measuring water in oil and will be described with particular reference thereto. It will be appreciated, however, that the invention is also amenable to other applications.

Analysis of water concentration in lubricating fluids for the power generation industry, heavy manufacturing and large equipment usage has been identified as a market for infrared spectrometers. A method for measuring water in oils by infrared spectroscopy is known. However, the known method does not accurately determine the concentration of water in all types of oil.

Measuring water in lubricating fluids is a relatively difficult analysis due to several factors. In turbine oils, water separates from the oil. In an extreme case, water forms a layer on the bottom of a sample container. In other cases, an oil sample looks cloudy due to small water droplets within the sample which scatter light. Typically, turbine oils can only hold about 50 to about 100 ppm of water in solution; greater amounts of water will typically either form small droplets or settle out.

The present invention provides a new and improved method and apparatus which addresses the above-referenced problems.

SUMMARY

A method for determining an amount of polar substance in a non-polar media includes adding a surfactant to increase a dispersion of the polar substance in the non-polar media and to increase the optical absorbance of the polar substance in the non-polar media to create a sample, passing an initial optical spectrum through the sample, measuring a resultant optical spectrum exiting the sample, relating the resultant optical spectrum to a predetermined quantitative calibration, and determining a concentration of the polar substance in the non-polar media based on the relation of the resultant optical spectrum to the quantitative calibration.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to exemplify the embodiments of this invention.

DETAILED DESCRIPTION OF ILLUSTRATED EMBODIMENT

Water content is an important measurement in all lubricants. Water can lead to reduction of oil's properties which in turn can lead to equipment failure. Turbine oil is a mineral oil based fluid which is highly hydrophobic by nature. In addition, some oils contain additives which by design force water out of the oil. A complicating factor is that some oils contain additives which help to dissolve water in the oil. Water can also adhere to sample container walls. Due to these multiple factors, different brands of turbine oil may absorb different amounts of water. It is generally accepted that turbine oil will absorb about 50 to about 200 ppm of water. At greater concentrations water exists as small droplets called micelles. For short amounts of time these droplets may be emulsified in the turbine oil, producing a cloudy appearance. These water droplets or micelles can also form layers in oil and are attracted to air bubbles formed during mixing. Water can also evaporate into the container head space after mixing. These issues are addressed in the turbine oil method described herein.

Figure 1:
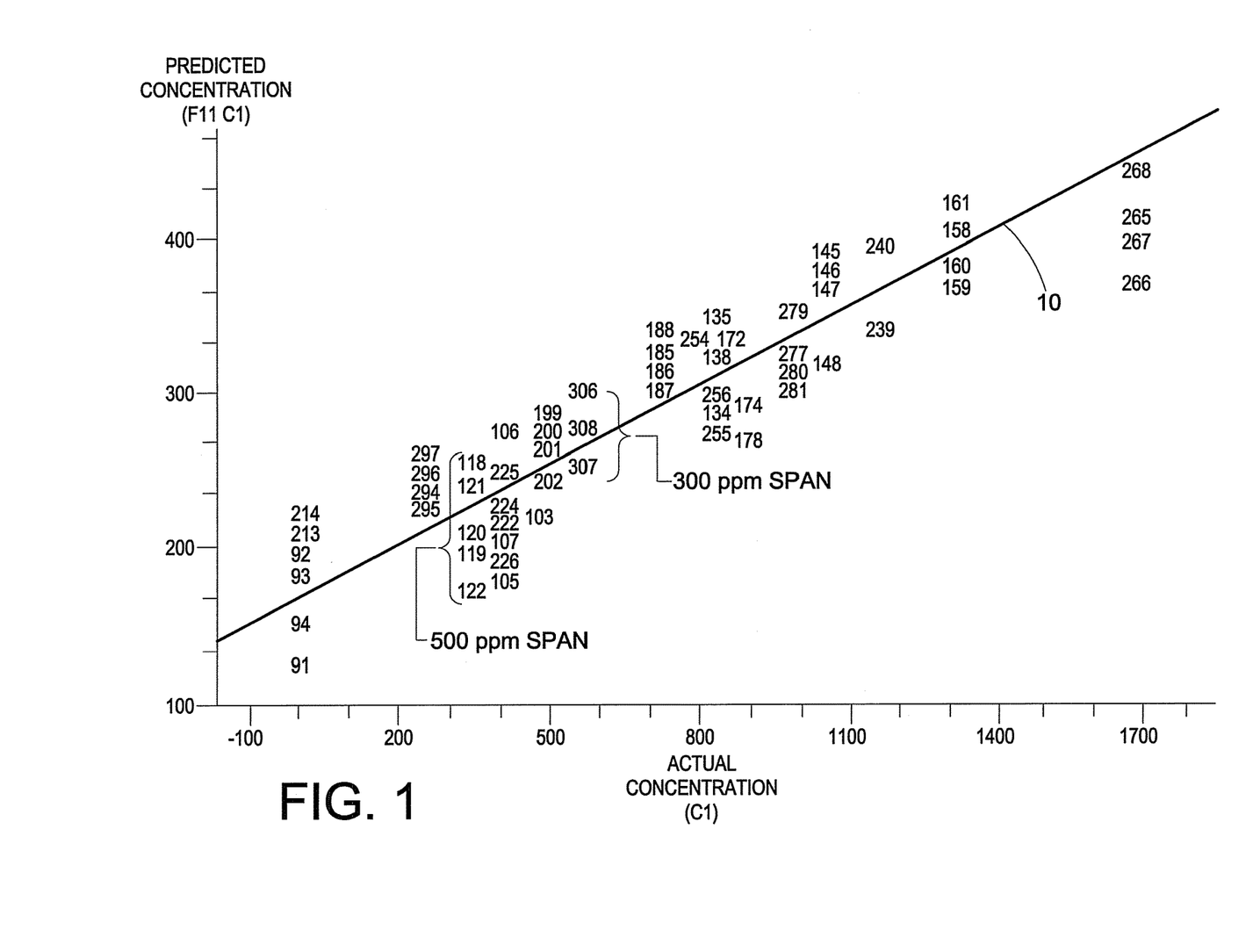
FIG. 1 illustrates a plot of predicted vs. actual values for water in turbine oils.

Conventional methods for measuring water in oil correlate the intensity of the infrared band due to the oxygen-hydrogen (OH) fundamental stretch of water near 3400 cm$^{-1}$ to the concentration of water in oil. Measurement of known concentrations forms a calibration. This calibration is then used to predict the concentration of an unknown sample measured in a similar way. If a single band intensity or area is used, this process is referred to as a univariate calibration. Similarly, a large area of the spectra can be used for correlation using multivariate techniques such a principle component regression (PCR) or partial least squared (PLS). Methods to measure water in oil directly by infrared spectroscopy were originally developed for lubricants with hydrophilic additives, such as motor oil; an example of these methods is specified in the ASTM standard E2412. These conventional methods, when used to measure water directly in turbine oil, produced inconsistent result among different types and/or brands of turbine oil. Variations of +/−40% have been observed on replicate measurements. This effect is most evident in turbine oil which has few additives that can solvate water; however, replicate measurements of other lubricants, such as gear, hydraulic or engine oil, show a similar variation. One problem with this initial method is variations in the spectral baseline. To address variations in the conventional method due to variation in the spectral baseline, the calibration was repeated using a multivariate algorithm (e.g., a partial least squares (PLS) algorithm or a principal component regression (PCR) algorithm). PLS can reduce effects of inconsistent spectral baselines on quantitative predictions. The PLS method still produced variation of greater than about 10% on replicate measurements (e.g., measurements of different portions (e.g., drops) of a sample). The results were investigated further to determine the source of the error. By dividing the calibration by different brands of oil, the magnitude of error was found to be dependent on the oil brand. Additive formulations in the different brands affected the solubility of water in the oil and hence the distribution of water droplets. A plot 10 showing the performance of the calibrations for two oil brands is shown in FIG. 1. The variation in the predicted concentration for multiple measurements of the same standard is between about 450 ppm to about 750 ppm for this convention method. For example, the three (3) measurements near the "300 ppm span" bracket are sample numbers 306, 307, and 308. These three all have an actual concentration of 600 ppm (x-axis). The 306 measurement's predicted concentration is about 750 ppm (y-axis), and the 307 measurement's predicted concentration is at about 450 ppm. Therefore, variation is about 300 ppm. This large variation makes this conventional method unsuitable for prediction of water concentration in lubricants.

Figure 2:
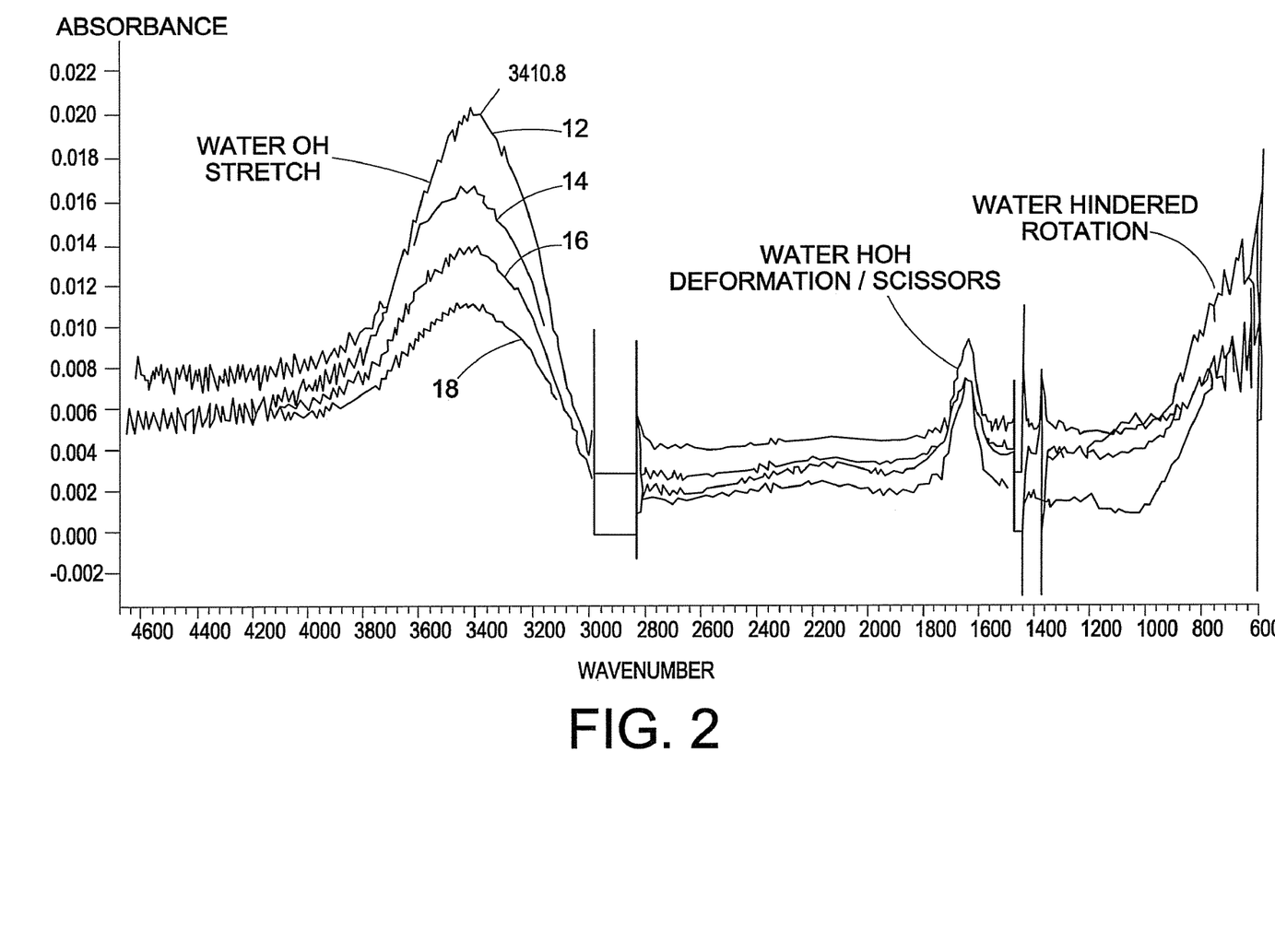
FIG. 2 illustrates plots of IR spectral subtraction overlay which is the basis for the conventional methodology.

Subtraction of the oil spectrum from replicate measurements of the same standard of water in lubricant shows a clear water spectrum for each sample; however, there are several differences between the replicates 12, 14, 16, 18 as is shown in FIG. 2. First, the water absorbance varies by up to a factor of three at a wavenumber of about 3400 in the replicate measurements and secondly, measurements which showed a lower water absorbance also showed a baseline shift characteristic with light scattering. The ratio of light which is scattered to the light which is absorbed is dependant on the size of water droplets in the oil, and only the absorbed light can be used to measure the amount of water present. According to the Rayleigh equation for scattering, particles or droplets with a diameter greater than $\frac{2}{3}$ the wavelength of light produce unacceptable scattering. Without reproducible dispersion of the water in the oil, the samples will not produce reproducible analytical results due to differences in the amount of absorbed versus scattered infrared light.

In order to improve the reproducibility of measuring water in turbine oil using infrared spectroscopy, a new methodology of measurement is used. The addition of a mixture of water stabilizers (e.g., surfactants) to the oil before the measurements has proven successful at eliminating the variability and other problems observed in the previous method. The surfactants of interest have a polar end which hydrogen bonds to the water and a non-polar aliphatic, alkyl aromatic, fluorinated, or chlorinated hydrocarbon end that dissolves fully into the oil. The surfactant mixture may contain non-ionic, cationic, or anionic surfactants. The polar end group may consist of 1-15 moles of ethylene oxide adduct, a substituted sorbitan oleate, or a sulfonate functional group (i.e., alkyl sulfosuccinate). Other polar end groups may be nitrogen or phosphate based, in which the resulting functional group can be a phosphate salt, a phosphoric acid or amino phosphoric acid, organo phosphate, amine, amine salt (i.e. tertiary or quaternary amines), or an alkyl ammonium complex. Perfluorinated surfactants also consist of a polar end group, such as carboxylic acids, sulfate, amine, or phosphate groups. The non-polar alkyl, alkylene group, or halogenated hydrocarbon may be C3-C32 in length with possible internal unsaturations. Silicone can replace the carbon atoms in the composition of the non-polar (hydrophobic) group and may be Si1-Si32 in length, an example of a silicone surfactant has a formula as follows: $R[-Si(CH3)2O-]x[(-CH2-CH2O-)nH]3$. The polar end groups for silicone based surfactants can be the same as those mentioned above for the carbon based surfactants, i.e. ethylene oxide chain, carboxylate, amino, phosphate, or sulfate. The surfactant mixture may also be complimented with oil soluble polymers/copolymers such as polyethylene oxide or polypropylene oxide, which have surface active properties. Some bio-friendly surfactants are made from amino acids and are referred to as sarcosides or alkyl amino acids; they consist of a fatty amide non-polar group and a carboxylate salt polar group. Other environmentally friendly surfactants are similar to and often derived from vegetable or animal oils/fats, and are called glycerol ester surfactants. Many derivatives of these glycerol ester surfactants can be made, including the reaction products of a fatty triglyceride with polyglycerol. All these types of surfactants will allow two active improvements to the water dispersion in oil. First, they will reduce the size of the water micelles to a diameter less than $\frac{2}{3}$ the analytical wavelength of light in the oil and thus reduce or eliminate the amount of scattered IR radiation. Secondly, the right surfactant composition will produce a narrow particle size distribution of water micelles, which will make the samples and IR measurements more consistent. The surfactant composition may also be tailored such that each water molecule is solvated with the surfactant thru hydrogen bonding interactions with the polar end group. This effectively solvates all the water in the oil/surfactant continuous phase and allows the IR radiation to interact with all the water in the sample. This allows for a more even distribution of water in the sample and produces prediction errors less than about 10%.

In one embodiment of the present invention, a method has been developed which includes the addition of about 3.2 wt % surfactant in a mixture of a non-polar substance (e.g., an oil such as turbine oil) and a polar substance (e.g., water). For example, about 0.5 mL of surfactant is added into a 4 dram vial of turbine oil or 3.175 mL surfactant (full sampling pipet) in a full 4 oz bottle of turbine oil. The addition of the surfactant causes the water micelles (microscopic droplets) to shrink to smaller sizes and suspends them substantially evenly throughout the oil. This act of suspending water in oil is called emulsification. Surfactants are surface active molecules that decrease the surface tensions of liquids. It is this property that inhibits water droplets from adhering to container walls or air bubbles. This produces a much more stable suspension (emulsion) of water in oil. Surfactants are often used as anti-foaming agents in turbine and gear oils. In addition to the making a stable emulsion, the surfactant may also allow some or all of the water to be completely solvated into the oil phase.

A method using surfactant stabilizers to measure water in turbine oil with a Fourier Transform Infrared Spectrometer (FTIR) was developed using two different turbine oil brands. Seventeen different concentration standards of water in turbine oil were measured on FT-IR spectrometers. The standards were prepared gravimetrically (by weight) in a range from 5-5300 ppm, using both new oil and used in-service oils. The surfactant was added by pipette and gently mixed (agitated) in a circular motion in order to prevent air bubbles from entering the sample. To confirm the water concentrations, the standards were measured by coulometric Karl Fischer (KF) titration shortly after the IR spectra were measured. The spectral data from each instrument and the KF results were used to develop a calibration based on partial least squares (PLS). The calibration used 3 factors with mean centering and baseline correction preprocessing. The calibration produced a standard error of cross-validation (SECV) of 85 and a correlation of R2=0.998 (see plot 20 in FIG. 3). The surfactant was found to contribute 25.5 ppm of water to each sample, which was therefore subtracted from the KF results prior to PLS method development. With reference to FIG. 3, which illustrates the plot 20 of predicted vs. actual values for water in oil including surfactant, the data points are noticeably closer along the plot 20 than in FIG. 1. Although a multivariate algorithm is discussed above, it is to be understood that univariate algorithms are also contemplated.

The method was validated with an independent validation set of standards prepared at 500 ppm, 1000 ppm, 2000 ppm, 3000 ppm, and 5000 ppm of water, with the surfactant added prior to the IR spectral analysis on four FTIR spectrometers. The average error of prediction for the validation set was 5%, and the prediction values from one of the instruments are compared to the KF values in Table 1 below. The relative standard deviation of the predictions are <2% (1000-5000 ppm) and <5% (500 ppm).

TABLE 1

The predicted water (ppm) in turbine oil (Infrared surfactant method) vs. the actual concentration determined by Karl Fischer analysis.

| Infrared prediction (ppm) | Actual Concentration (by Karl Fischer) (ppm) | Difference (ppm) | % Error |
| --- | --- | --- | --- |
| 508 | 504 | 4 | 0.8 |
| 1054 | 965 | 89 | 9.2 |
| 2043 | 2002 | 41 | 2.0 |
| 2946 | 2838 | 108 | 3.8 |
| 4710 | 4753 | 43 | 0.9 |

Figure 3:
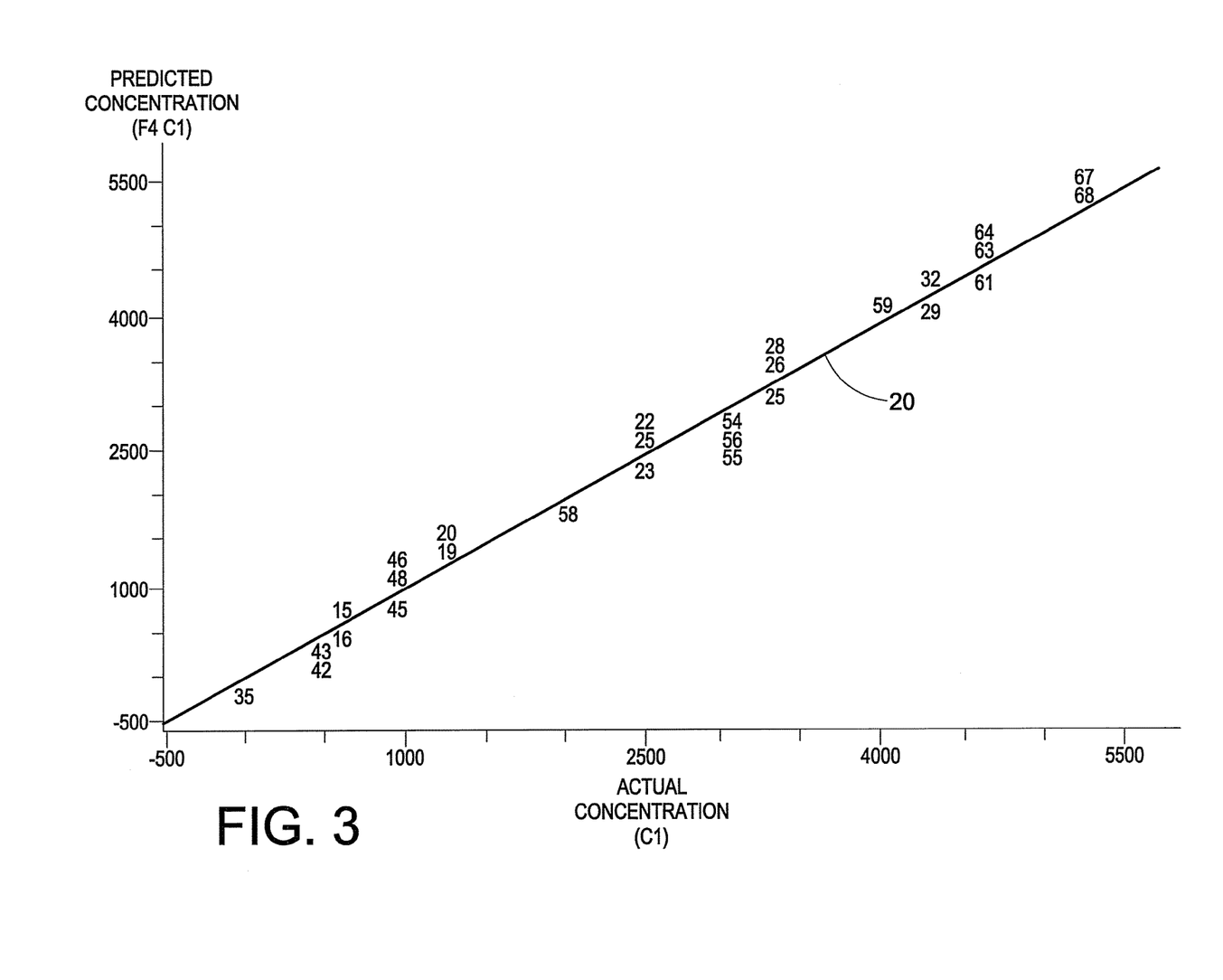
FIG. 3 illustrates a plot of predicted vs. actual values for water in turbine oils including water stabilizers.
Figure 4:
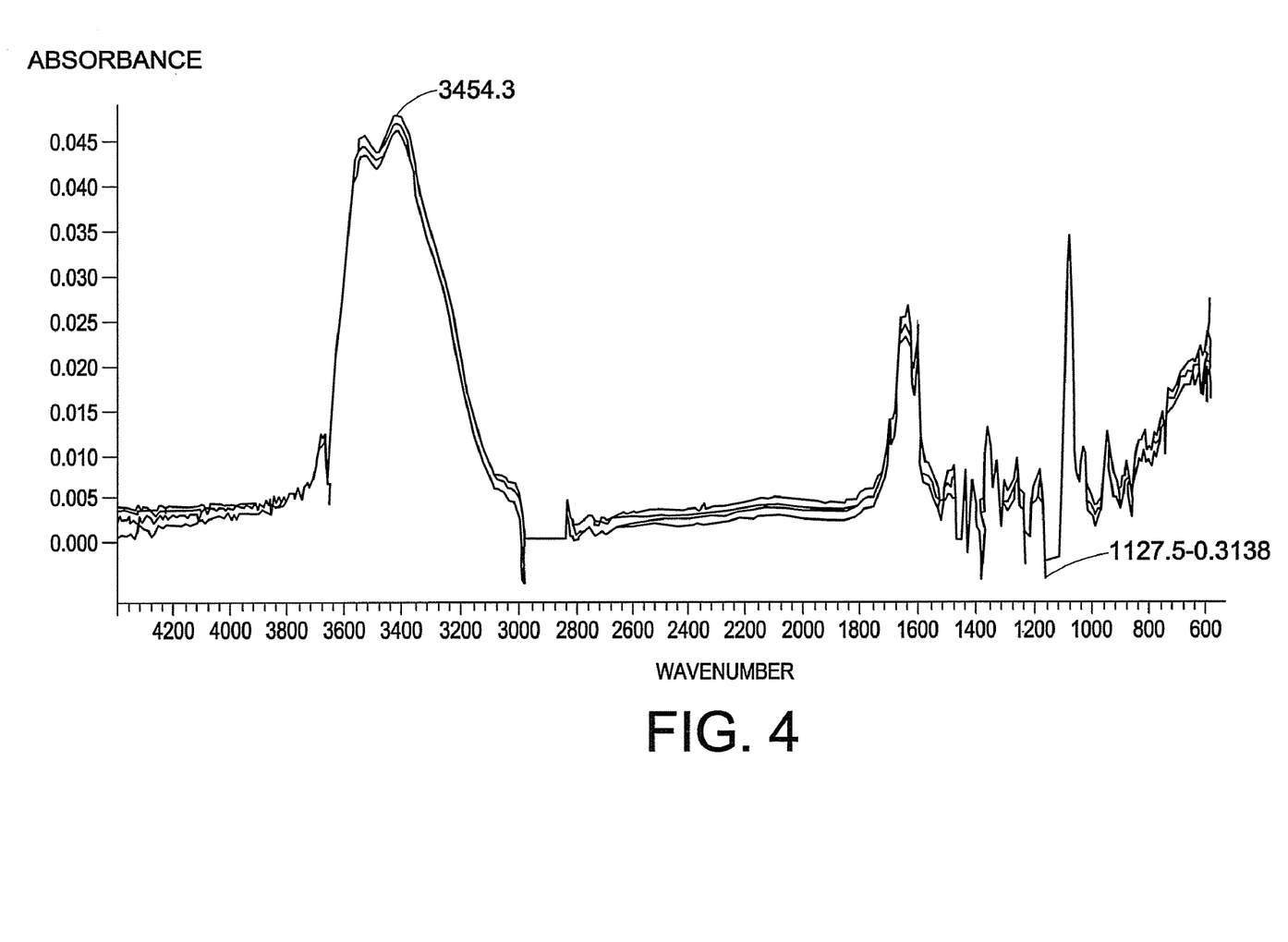
FIG. 4 illustrates plots of IR spectral subtraction overlay from different instruments.
Figure 5:
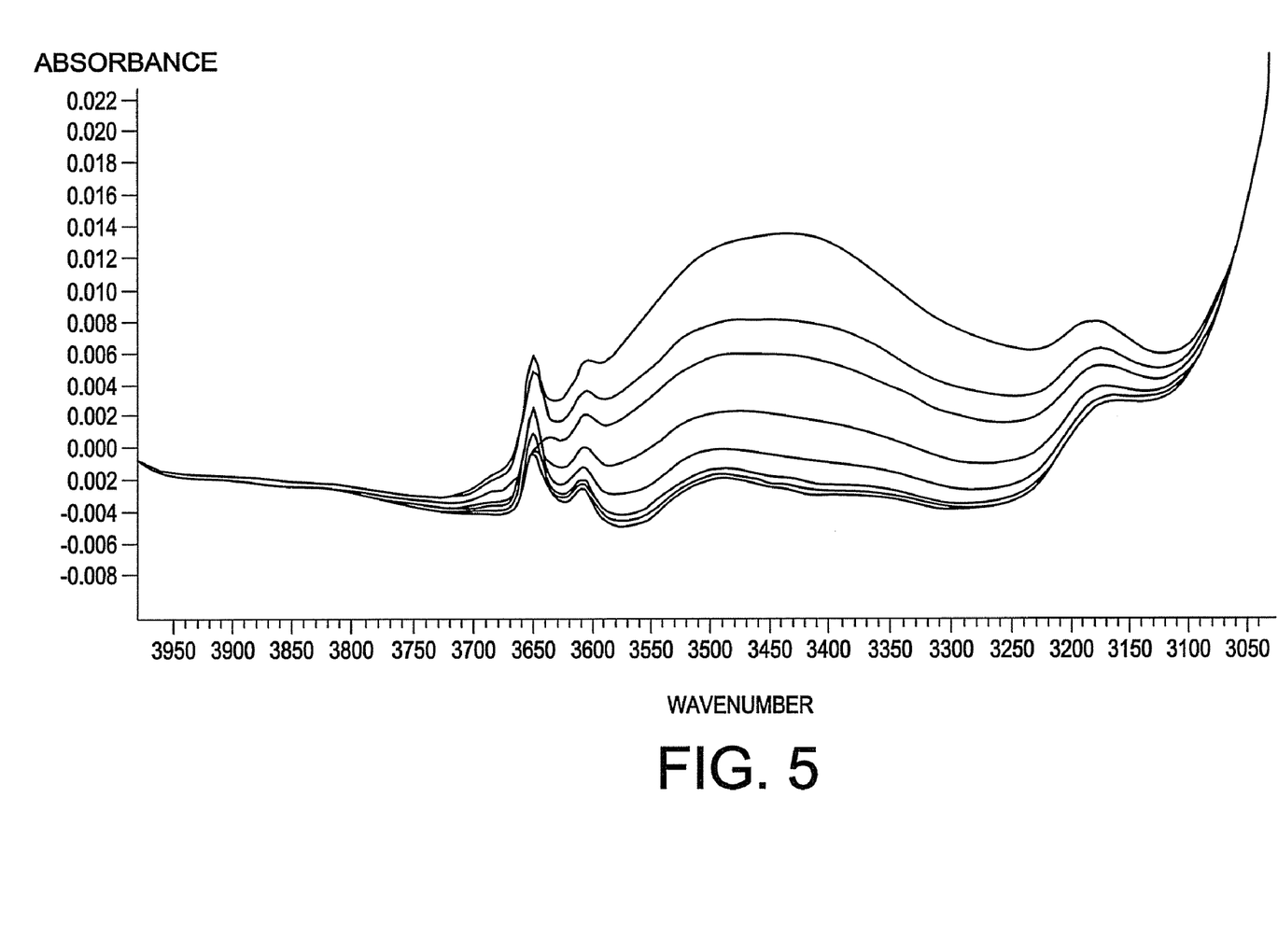
FIG. 5 illustrates IR spectral overlay of water in turbine oil including a water stabilizer.
Figure 6:
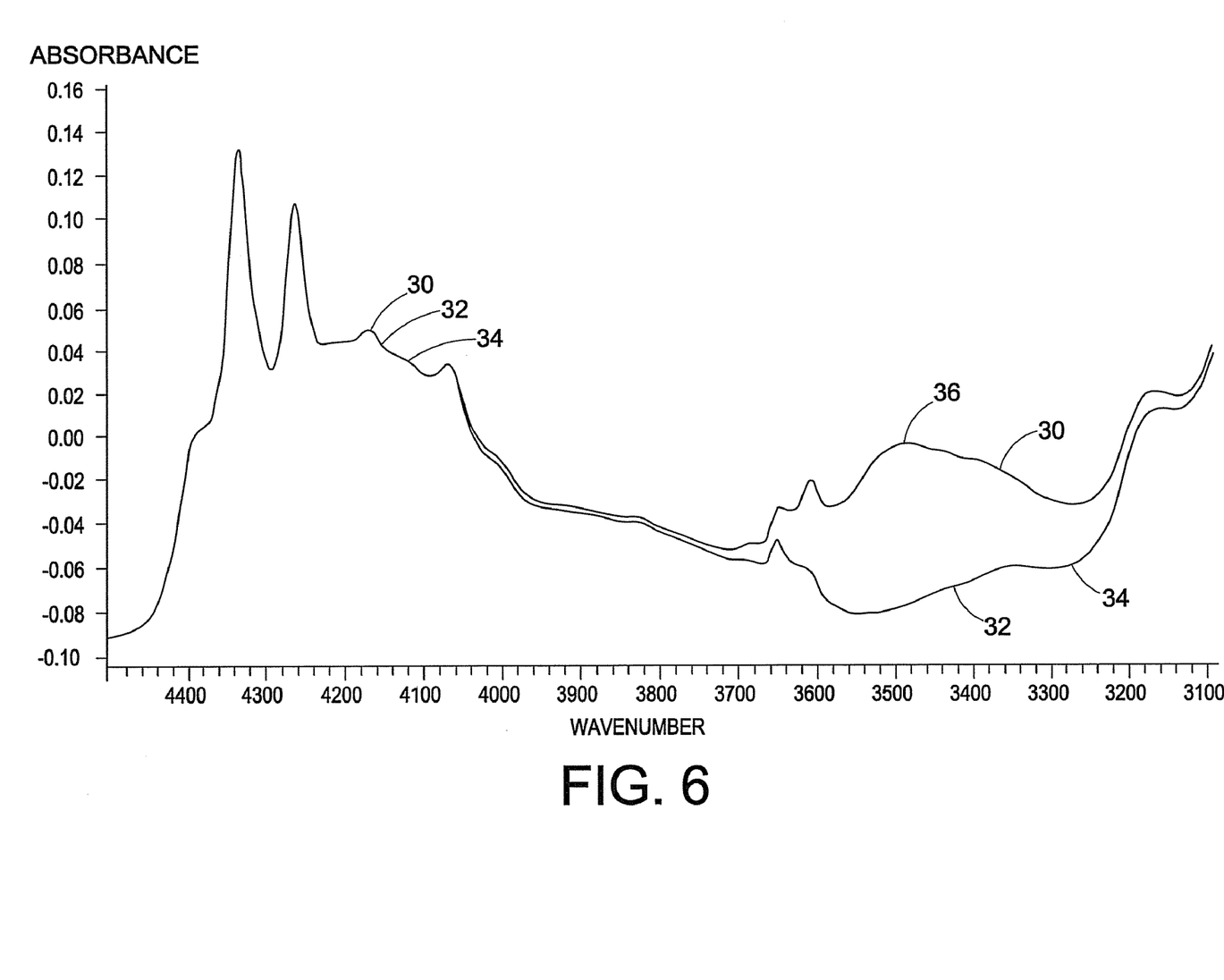
FIG. 6 illustrates plots of absorbance vs. wave number for various samples.

Issues related to reproducibility and accuracy observed in the non-surfactant method have been reduced or eliminated in this surfactant stabilized method. The advantage in using this new surfactant stabilized method is shown in the prediction results on the validation set and is seen by comparing the actual vs. predicted plots in FIGS. 1 and 3. The new method shows about a three-fold increase in water absorbance. With reference to FIG. 4, little variation is seen between replicate measurements of a 1300 ppm standard of water in oil which has been surfactant stabilized. The spectrum of the base oil was subtracted from each of the displayed spectra to emphasize the water absorbance. Comparison of FIG. 4 (surfactant stabilized) to FIG. 2 (conventional method) shows the water absorbance to be less variable in the surfactant stabilized method. Further, the average absorbance of the water band at about 3500 cm$^{-1}$ is about 0.047 (FIG. 4) in the surfactant stabilized method; this is about three times greater than the highest absorbance for the conventional method (FIG. 2). The quality of this calibration can also be observed in the clean incremental increase in water absorbance band near 3400 cm$^{-1}$ throughout the calibration spectra (FIG. 5). With reference to FIG. 6, spectra lines 30, 32, 34 of absorbance vs. wavenumber are illustrated from samples with 1,120 ppm (0.112%) H$_2$O added in oil. The spectrum line 30 represents the line achieved when a surfactant is added to an oil and water mixture as discussed above. The spectrum line 32 represents an oil and water mixture without a surfactant added. The spectrum line 34 represents an oil alone (with no water added) without a surfactant added. The spectrum line 30 shows a relative peak 36 at about 3,500 wavenumber due to the fundamental oxygen-hydrogen (OH) stretching vibration of water. This relative peak 36 results from a relatively higher intense absorbance than the spectrum line 32. Spectrum line 34 shows no absorbance band at about 3500 wavenumbers, because no water is present in that sample. As discussed above, only the absorbed light can be used to measure the amount of water present in a water and oil mixture. Therefore, the relatively higher absorbance of the spectrum line 30 indicates more sensitive measurements of water in a water and oil mixture are achieved when a surfactant is added to the oil and water mixture.

Figure 7:
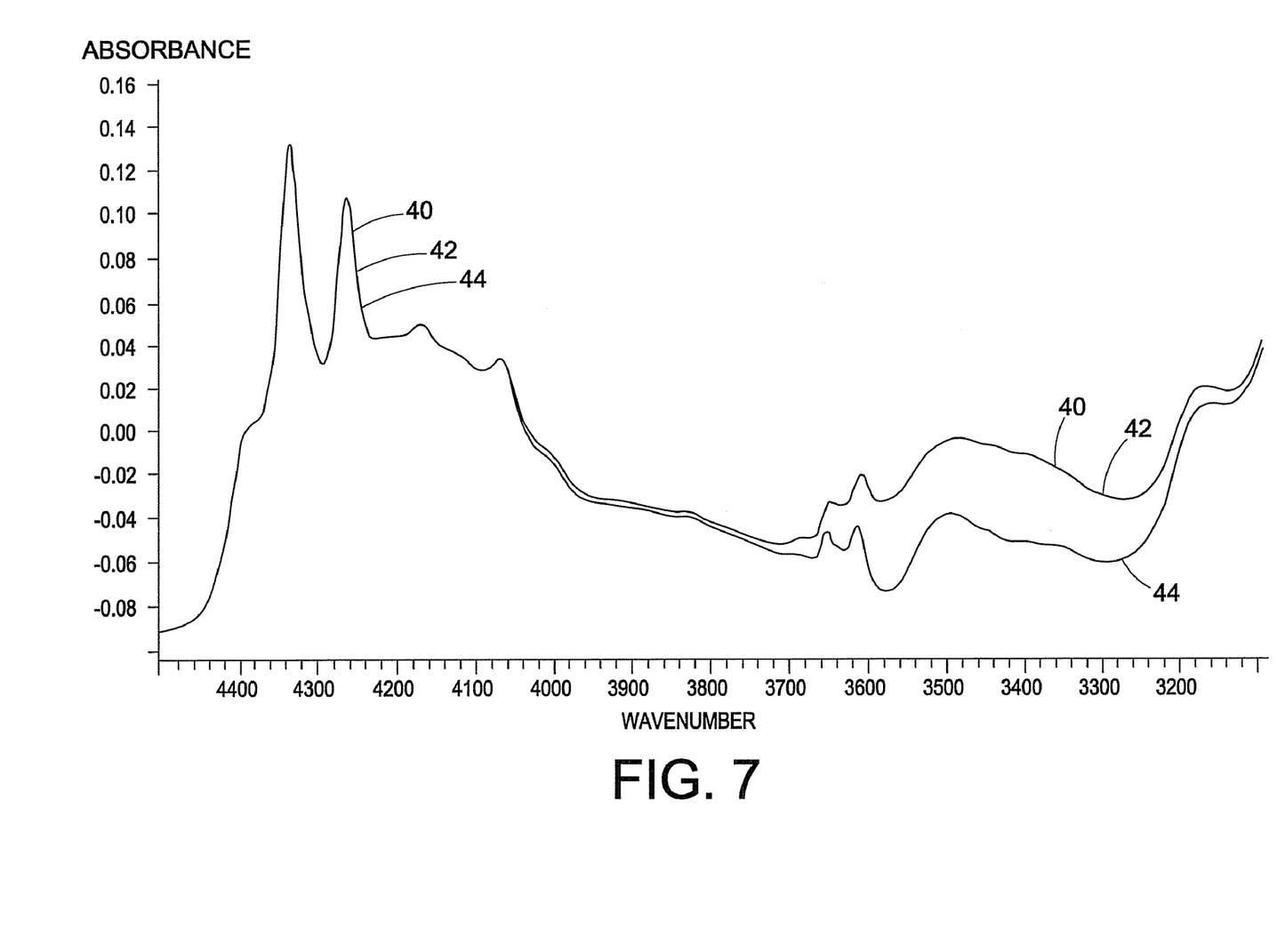
FIG. 7 illustrates plots of absorbance vs. wave number after various time delays.

With reference to FIG. 7, spectra lines 40, 42, and 44 of absorbance vs. wavenumber are illustrated from samples containing oil with the surfactant added as discussed above. The 40 and 42 spectra lines represent samples also including 1,120 ppm water. The spectrum line 40 is measured two (2) minutes after sample preparation and the spectrum line 42 is measured 30 minutes after sample preparation. The spectrum line 40 and spectrum line 42 substantially overlay each other. The spectrum line 44 line represents a control sample including only the oil and surfactant with no water.

As illustrated in FIG. 7, water measurement is not significantly affected by a 2-30 minute time delay after sample preparation. As shown in Table 2, for a 1,175 ppm standard with a 2 minute wait time after adding the surfactant provides substantially similar results compared to the longer 20-30 minute delays. Results from a similar test conducted using the conventional method without the surfactant as a water stabilizer are shown in the right most column of Table 2; the results are not as consistent and the method is less robust. Using the surfactant as a water stabilizer produces a variation in predicted water concentration of less than 3% over the time period of 30 minutes, while the conventional method produces an error of up to 20% over the same time period.

TABLE 2

Measurement results of water in turbine oil for 1175 ppm standard for both surfactant method and conventional method showing the effect of a time delay between sample preparation and analysis.

| Time (minutes) | Predicted Value - Surfactant Method (ppm) | Predicted Value - Conventional Method (ppm) |
| --- | --- | --- |
| 2 | 1139 | 1427 |
| 5 | 1171 | 1257 |
| 10 | 1166 | 1141 |
| 20 | 1156 | 999 |
| 30 | 1196 | 952 |

In one embodiment of the present invention, a method is contemplated for determining an amount of polar substance (e.g., water) in a mixture in a non-polar media (e.g., oil). In one embodiment, the oil is a turbine oil such as Chevron GST 32 and Mobil DTE 797. The method includes obtaining the mixture and creating a sample by adding a water stabilizer (e.g., surfactant) to the mixture to achieve a predetermined percentage by weight of the surfactant in the mixture. In one embodiment, the predetermined percentage by weight of the surfactant in the mixture is empirically determined to produce the highest spectral response in the desired concentration range. An initial optical spectrum is passed through the sample, and a resultant optical spectrum exits the sample. The resultant optical spectrum is measured and related to a quantitative calibration. A concentration of the polar substance in the non-polar media based on the relation of the resultant optical spectrum to the quantitative calibration.

Use of a surfactant to stabilize polar analytes (such as water) in non-polar solutions improves the measurement of that analyte through improved sampling. In all analytical methods, a representative sample must be introduced to the detection technology. This is truly independent of the detection mechanism. Stabilizing the polar analyte through use of a surfactant as a pretreatment step increases the likelihood that a true, representative sample will be measured. Table 3 shows that the surfactant (water stabilizer) technology discussed above improves the accuracy of coulometric Karl Fischer measurements. The table compares the results obtained by repetitive Coulometric Karl Fischer measurements of a standard containing 1175 ppm water in turbine oil. The standard was prepared in duplicate and measured by Karl Fischer with and without the water stabilizer. Using the water stabilizer reduces the average error of this measurement in the same way in which it reduced the average error of the infrared measurement. Independent of the detection technology (Karl Fischer or infrared spectroscopy), addition of a surfactant as a pre-treatment step improves the sample homogeneity and therefore the analytical result.

TABLE 3

Coulometric Karl Fischer results on a gravimetrically prepared 1175 ppm water in turbine oil standard measured with and without water stabilizer additive.

| | No Water Stabilizer, KF Water (ppm) | With Water Stabilizer, KF Water (ppm) |
| --- | --- | --- |
| Repeat 1 | 1045 | 1121 |
| Repeat 2 | 1021 | 1101 |
| Repeat 3 | 1085 | 1092 |
| Average | 1050 | 1105 |

It is contemplated that the initial optical spectrum (and the resultant optical spectrum) is ultraviolet light, visible light, near-infrared light, infrared light, and Raman optical spectrum through the sample.

The surfactant stabilized turbine oil method produced reproducible results. The calibration has provided reproducible results in a validation set and has reduced, or even eliminated, the variation in water absorbance observed in the conventional method for measurement of water in turbine oil by infrared spectroscopy or other measurement techniques. The method was built to withstand a reasonable amount of variation in surfactant concentration. Other surfactants could also be identified to further improve the method. The use of surfactants to solvate water and/or manipulate micellar sizes in a reverse emulsion to increase direct electromagnetic radiation interaction of liquid particulates is a novel application and is applicable to other markets within and beyond oil analysis. Other optical spectroscopic techniques suffer similar issues with scattering and fluorescence when the analyte of interest exist in various sized micelles in another liquid. These developments relate to the use of surfactants to either solvate water or stabilize micelle size in order to improve spectroscopic quantitative methods for many types of immiscible liquids including but not limited to both water in oil and oil in water. This technique provides the ability to make these measurements quickly and reproducibly.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

We claim:

1. A method for determining, an amount of polar substance in a non-polar media, the method comprising:
    adding a surfactant to increase a dispersion of the polar substance in the non-polar media and to increase the optical absorbance of the polar substance in the non-polar media to create a sample;
    passing an initial optical spectrum through the sample;
    measuring a resultant optical spectrum exiting the sample;
    relating the resultant optical spectrum to a predetermined quantitative calibration; and determining a concentration of the polar substance in the non-polar media based on the relation of the resultant optical spectrum to the quantitative calibration.

2. The method as set forth in claim 1, further including, before the measuring step:
    delaying at least 20 minutes.

3. The method as set forth in claim 1, further including:
    creating the quantitative calibration.

4. The method as set forth in claim 3, wherein the step of creating a quantitative calibration includes:
    correlating at least one of band intensity and area to known analyte concentrations using a univariate technique.

5. The method as set forth in claim 3, wherein the step of creating, a quantitative calibration includes:
    establishing a correlation between spectral data and known analyte concentrations using a multivariate technique.

6. The method as set forth in claim 1, wherein the passing step includes one of:
    passing an initial ultraviolet optical spectrum through the sample;
    passing an initial visible optical spectrum through the sample;
    passing an initial near-infrared optical spectrum through the sample;
    passing an initial infrared optical spectrum through the sample; and
    passing an initial Raman optical spectrum through the sample.

7. The method as set forth in claim 6, wherein the measuring step respectively includes one of:
    measuring a resultant ultraviolet optical spectrum exiting the sample;
    measuring a resultant visible optical spectrum exiting the sample;
    measuring a resultant near-infrared optical spectrum exiting the sample;
    measuring a resultant infrared optical spectrum exiting the sample; and
    measuring a resultant Raman optical spectrum exiting, the sample.

8. The method as set forth in claim 1, further including:
    producing inverse micelles, as a result of the addition of the surfactant, for producing a substantially homogeneous mixture of the polar substance in the non-polar media.

9. The method as set forth in claim 1, wherein the determining step includes:
    determining a concentration of water in oil based on the relation of the resultant optical spectrum to the quantitative calibration.

10. The method as set forth in claim 1, further including:
    distributing the surfactant within the polar substance within the non-polar media.

11. The method as set forth in claim 1, further including:
    creating the surfactant to include a polar end which hydrogen bonds to the polar substance and a non-polar aliphatic, alkyl aromatic, silicone, perfluorinated or chlorinated hydrocarbon end that dissolves fully into the non-polar substance.

12. A sample to be measured for determining an amount of a polar substance in a non-polar media, the sample comprising:
    a polar substance;
    a non-polar media, the polar substance and non-polar media creating a mixture; and
    a predetermined percentage of a surfactant in the mixture to increase a dispersion of the polar substance in the non-polar media and to increase an optical absorbance of the polar substance in the non-polar media to create a sample, a concentration of the polar substance in the non-polar media being determined based on a relation of a resultant optical spectrum exiting the sample to a quantitative calibration.

13. The sample as set forth in claim 12, wherein, the polar substance is water.

14. The sample as set forth in claim 13, wherein the non-polar substance is oil.

15. The sample as set forth in claim 12, therein the predetermined percentage of the surfactant in the mixture is about 3.2 wt % surfactant.

16. The sample as set forth in claim 15, wherein:
the surfactant includes a polar end which hydrogen bonds to the polar substance and a non-polar aliphatic, alkyl aromatic, perfluorinated or chlorinated hydrocarbon end that dissolves fully into the non-polar substance.

17. The sample as set forth in claim 16, wherein:
the surfactant contains non-ionic, cationic, or anionic surfactants;
the polar end group consists of 1-15 moles of ethylene oxide adduct, a substituted sorbitan oleate, alkyl-amine, alkyl-ammonium, sarcoside, amino acid, glycerol esters or derivatives, carboxylate, phosphate, amino phosphoric acid, phosphoric acid, or sulfonate functional group; and
the non-polar aliphatic, alkyl aromatic, silicone, perfluorinated or chlorinated hydrocarbon group is C3-C32 in length or Si1-Si32 in length for silicone based surfactants.

18. The sample as set forth in claim 12, wherein the surfactant settles in the mixture for about 20 minutes to create the sample.

19. The sample as set forth in claim 12, wherein:
the relative amounts of the polar substance and the water in the sample are determined as a ratio of an amount of mid-infrared light exiting the sample to an amount of the mid-infrared light entering the sample.

20. The sample as set forth in claim 12, wherein:
the sample has a water absorbance of about three times greater than a same sample measured under similar conditions without the surfactant.

21. The sample as set forth in claim 12, wherein:
an infrared optical spectrum passes through the sample to create the resultant optical spectrum.

* * * * *

UNITED STATES PATENT AND TRADEMARK OFFICE
CERTIFICATE OF CORRECTION

| | |
|---|---|
| PATENT NO. | : 8,068,218 B2 |
| APPLICATION NO. | : 12/422817 |
| DATED | : November 29, 2011 |
| INVENTOR(S) | : Frank S. Higgins et al. |

It is certified that error appears in the above-identified patent and that said Letters Patent is hereby corrected as shown below:

In column 7, line 58, in Claim 1, delete "determining," and insert -- determining --, therefor.

In column 8, line 14, in Claim 5, delete "creating," and insert -- creating --, therefor.

In column 8, line 39, in Claim 7, delete "exiting," and insert -- exiting --, therefor.

In column 9, line 6, in Claim 13, delete "wherein," and insert -- wherein --, therefor.

In column 9, line 11, in Claim 15, delete "therein" and insert -- wherein --, therefor.

In column 9, line 16, in Claim 16, after "aromatic," insert -- silicone, --.

Signed and Sealed this
Tenth Day of January, 2012

David J. Kappos
*Director of the United States Patent and Trademark Office*